United States Patent [19]

Yamada

[11] Patent Number: 4,588,408
[45] Date of Patent: May 13, 1986

[54] TREATED HAIR FOR IMPLANTATION

[76] Inventor: Shiro Yamada, No. 31-8, Koboyama, Kobo-cho, Chiryu-shi, Aichi-ken, Japan

[21] Appl. No.: 418,454

[22] Filed: Sep. 15, 1982

Related U.S. Application Data

[63] Continuation-in-part of Ser. No. 132,176, Mar. 20, 1980, abandoned.

[30] Foreign Application Priority Data

| Mar. 29, 1979 | [JP] | Japan | 54-40005 |
| Mar. 29, 1979 | [JP] | Japan | 54-40006 |
| Mar. 25, 1980 | [CA] | Canada | 3481399 |
| Mar. 25, 1980 | [DE] | Fed. Rep. of Germany | 3011520 |
| Mar. 27, 1980 | [GB] | United Kingdom | 8010401 |
| Mar. 31, 1980 | [FR] | France | 8007222 |

[51] Int. Cl.⁴ .............................. A61F 1/00
[52] U.S. Cl. .............................. 623/15; 128/1 R
[58] Field of Search ............. 128/330, 1 R; 3/1; 623/15

[56] References Cited

U.S. PATENT DOCUMENTS

| 3,003,155 | 10/1961 | Mielzynski et al. | 623/15 |
| 3,858,245 | 1/1975 | Nate, II et al. | 623/15 |
| 3,998,230 | 12/1976 | Miller | 623/15 |
| 4,126,124 | 11/1978 | Miller | 623/15 |
| 4,382,444 | 5/1983 | Malmin | 3/1 |

FOREIGN PATENT DOCUMENTS

| 7629756 | 3/1977 | Fed. Rep. of Germany . |
| 2758907 | 12/1977 | Fed. Rep. of Germany . |
| 2843101 | 4/1979 | Fed. Rep. of Germany | 3/1 C |
| 2843072 | 4/1979 | Fed. Rep. of Germany . |
| 2912043 | 1/1980 | Fed. Rep. of Germany | 3/1 C |
| 1587858 | 2/1970 | France . |
| 2372621 | 6/1978 | France . |
| 2405702 | 5/1979 | France . |
| 2405703 | 5/1979 | France . |
| 2452281 | 5/1979 | France . |
| 2006018 | 5/1979 | United Kingdom . |

Primary Examiner—Richard J. Apley
Assistant Examiner—David Isabella
Attorney, Agent, or Firm—Browdy & Neimark

[57] ABSTRACT

A treated hair to be implanted in the human skin is produced such that the lower portion thereof is turned to form a looped portion which has its end portion protruding at an acute angle from a hair proper and such that the intersection thereof with the hair proper is fixed by a fusing process. The treated hair may be an artificial hair made of a thermoplastic synthetic resin. The treated hair thus produced may be made up of two hair components fixed in parallel to each other but separated substantially at the hair proper from each other.

8 Claims, 7 Drawing Figures

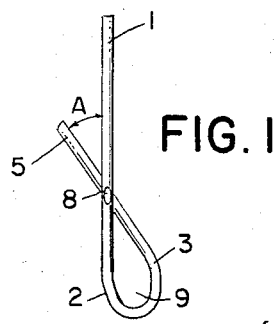
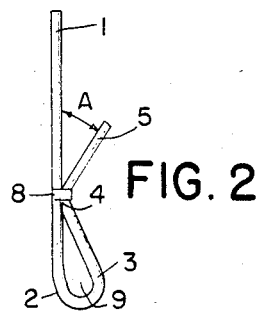
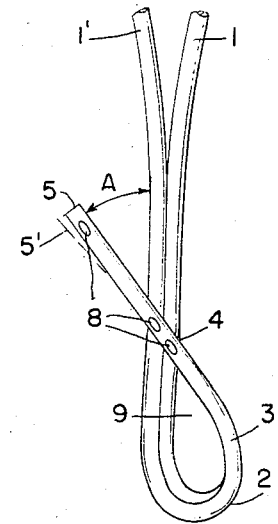
FIG. 1
FIG. 2
FIG. 3
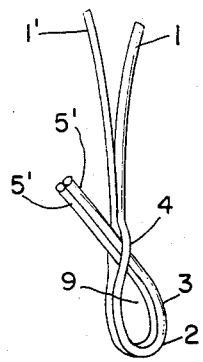
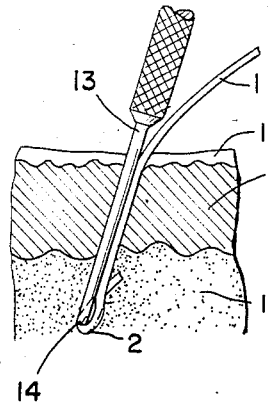
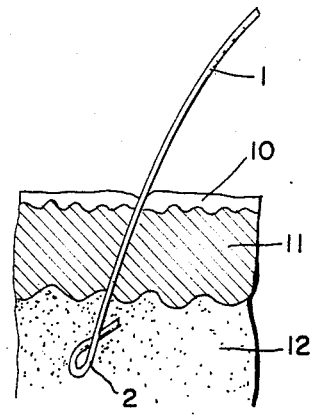
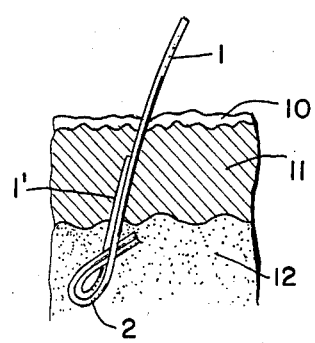
FIG. 4
FIG. 5
FIG. 6
FIG. 7

TREATED HAIR FOR IMPLANTATION

This is a CIP of parent co-pending application Ser. No. 132,176 filed Mar. 20, 1980, now abandoned the description of the invention of which is incorporated herein.

The present invention relates to improvements in a treated hair to be implanted directly in a human skin.

Recently, a variety of treated hairs to be implanted directly in a human skin have been developed and put into partial practice. Among them, especially, improvements in the shapes of the root portions of the hairs for enhancing the fixation of the hairs implanted have been proposed in various manners. One of the proposals can be found in U.S. Pat. No. 3,005,155 (F. C. Mielzynski et al.), in which artificial hairs having arrowhead-shaped root portions are disclosed. Formations of the root portions having such shape not only require remarkably high working techniques but also make it quite difficult to reduce the size of the root portions produced to a lower level than a preset limit.

The present inventor has actually implanted artificial hairs having root portions of various shapes for purposes of comparing and investigating them. According to the results revealed, we have found that minimization of the size of a wound to be caused in the human skin is the most important factor for enhancing the fixity of the hairs immediately after their implantations although formations of the root portions into such shapes as will resist highly their extractions is also important. It is therefore the greatest problem to form the root portions of hairs to be implanted into such shapes as can resist highly extractions and at the same can minimize their maximum cross-sectional areas on which is greatly dependent the size of the wound to be caused thereby.

From the points of view thus far described, there has been recently proposed a method, in which one end of an artificial hair made of a synthetic resin is turned to form a loop and is knotted to form a root portion. This method is economically excellent as a method of forming the root portion without complex processing such as an elastic working process. That method is, however, disadvantageous in that the knot is liable to come loose and has to be larger than the diameter of the hair root portion to such an extent as to enlarge the wound to be caused during the implantation so that the hairs implanted fall out in a high percentage. In addition, hair roots with such knots provides sites for serious infection and, in addition, if it becomes necessary to remove the hair, tissue which is grown around such knots make it difficult and indeed close to impossible to remove such hair without damage to the scalp.

The present invention is, therefore, improved to eliminate the aforementioned disadvantages.

SUMMARY OF THE INVENTION

It is an object of the present invention to provide a treated hair which is formed with such a root portion as is suitable for direct implantation in a human skin.

Another object of the present invention is to provide such a treated hair at a low cost and through a simple process as is formed with a root portion having a good fixation.

A further object of the present invention is to provide a treated hair formed with a root portion which is suitable for being implanted in a human skin by the use of an implanting needle having a bifurcated tip.

In order to attain these and other objects, there is provided a treated hair for implantation comprising: a hair proper for protruding from a human skin when said treated hair is implanted therein; and an unknotted root portion for being buried in the human skin when said treated hair is implanted therein, said root portion extending and turned from said hair proper for forming such a looped portion as has its end portion protruding therefrom at an acute angle at its intersection where it is fixed by fusion thereto.

According to the treated hair for implantation, the cross-sectional area of the root portion is so small that the wound to be caused during the implantation can be so reduced as to enhance remarkably the fixation of the hair implanted.

Moreover, since the wound is limited in extension, restoration therefrom is so fast that little secondary difficulty such as inflammation can be found. In addition, the fused intersection forming the hair root loop is weaker than the strength of the hair itself, so that by application of a certain force to the hair, the entire hair including the root can be removed from the scalp, when necessary, without damage to the scalp.

BRIEF DESCRIPTION OF THE DRAWINGS

FIG. 1 shows a treated hair exemplifying the present invention in its front elevation.

FIGS. 2 to 4 are front elevations showing other embodiments of the present invention;

FIG. 5 is an explanatory view showing a method of implanting the treated hair according to the present invention; and FIGS. 6 and 7 are explanatory views showing the conditions under which the treated hair is implanted.

DESCRIPTION OF THE PREFERRED EMBODIMENTS

The treated hair for implantation according to the present invention will be described in connection with the embodiments thereof with reference to the accompanying drawings.

As shown in FIGS. 1 and 2, the treated hair for implantation according to the present invention is produced such that the lower portion thereof is turned to form a looped portion 3 which has its end portion 5 protruding at an acute angle (A) from a hair proper 1 and such that the intersection 4 thereof with the hair proper 1 if fixed by fusion thereby to form a root portion 2 having a water-droplet shaped open loop 9.

In this embodiment, the hair proper 1 and the end portion 5 intersect obliquely to form the intersection 4. In other embodiments, as shown in FIG. 2, the end portion 5 may be bent at the intersection 4 in a manner to protrude such that the acute angle (A) is made between the hair proper 1 and the end portion 5. In these embodiments, the intersection 4 may be adhered by fusion at numeral 8 in FIGS. 1 and 2.

The treated hair may also be made up of two hair components which are fixed in parallel to each other but which are separated substantially at the hairs proper 1 and 1' from each other, as shown in FIGS. 3 and 4. In this embodiment, the lower portions of the hair components are turned together to form the looped portion 3 which has its end portions 5 and 5' protruding at the acute angle (A) form the hair propers 1 and 1' and the end portions 5 and 5' are fused at the intersection 4 to the hairs proper 1 and 1', as shown at 8, thereby forming the root portion 2 having a water-droplet shaped open loop 9.

In the embodiment shown in FIG. 3, moreover, the end portions 5 and 5' are turned to protrude around the surfaces of the hairs proper 1 and 1'. In the embodiment shown in FIG. 4, however, the end portions 5 and 5' may be made to protrude between the hairs proper 1 and 1'. In any of these embodiments, the end portions 5 and 5' and the hair propers 1 and 1' are fixed while interposing the others inbetween so that their fixed portions can be free from coming loose with the advantageous result that the resistance is reduced when the root portion 2 is forced into the human skin.

Since the treated hairs according to the embodiment thus described with reference to FIGS. 3 and 4 are respectively formed with the two hairs proper 1 and 1' for each root portion 2, the result is that two hairs are implanted by the single operation. In case, however, it is felt unnatural that the two hairs come out of each pore of a portion of the skin, e.g., a forehead, one of the hair propers may be cut at a position in the vicinity of the root portion 2, as shown in FIG. 7.

On the other hand, the end portions 5 and 5' are made to have a function as a hook for preventing the hair or hairs from coming out. In this regard, since the two end portions 5 and 5' are fixed, and may be coated as shown at numeral 6, the treated hair having the two component structure is markedly strong and is especially excellent in the effects for preventing the hairs from coming out.

The treated hair to be used may be either a human hair the root portion at least of which is coated with a fusible plastic, or preferably an artificial hair of a monofilament made of a synthetic resin such as polyamides, polyesters, polyvinyl chlorides, polyethylenes or polypropyenes. Especially, in the former case, the human hair has to be formed at its lower portion with the root portion, while confirming its orientation, after it is defatted in advance with caustic soda.

In case, moreover, human hair is used, it is eroded by the physiological action after it has been implanted. This makes it necessary to form the protecting coating on the surface of the root portion 2 and on the surface of the hair proper 1 in the vicinity of the former. Even in the case of the artificial hair, it is also preferred that the protecting coating is formed to reinforce the adhered portion and to increase the strength of the end portion 5.

An aqueous solution of polyvinyl alcohol or a coating forming material, in which polystyrene or polyamides are dissolved in a suitable solvent, is enumerated as a suitable material for the protecting coating.

In accordance with the invention, wherein the artificial hair is made of a thermoplastic synthetic resin such as polyethylene, polypropylene, polyester or polyvinyl chloride, or is coated with such a fusible plastic, the intersection 4 and its vicinities are fixed at the portion 8 by fusion. This fusing process is desirably effected by welding, most preferably without any difficulty by high-frequency point-welding techniques.

The root portion 2 thus formed according to the present invention is composed mainly of the looped portion 3 having a shape of a water droplet and the protruding end portion 5, but is made very small such that the maximum and minimum outside diameters of the looped portion 3 are 0.65 to 1.5 mm and 0.4 to 1.1 mm, respectively, e.g. 0.95 mm and 0.5 mm, and that the length of the end portion 5 is 0.4 to 1.2 mm, e.g. 0.6 mm.

On the other hand, the open loop 9 of the looped portion 3 is formed in its inside, which is intended partly to receive the bifurcated tip of an implanting needle during the implanting operation and partly to prevent the treated hair from coming out after the implanting operation.

As shown in FIG. 5, more specifically, the implanting needle 13 is used to clamp the lower end of the looped portion 3 of the root portion 2 at its bifurcated tip 14 thereof and is then to force the root portion into a hypodermal tissue 12 through a epidermis 10 and a dermal tissue 11. If only the implanting needle 13 is then pulled softly, the root portion 2 is left as it is in the hypodermal tissue 12, as shown in FIG. 11, because its protruding end portion 5 protrudes at the acute angle (A) from the hair proper 1 thereby to prevent the hair as a whole from coming out. If the wound closes after several days so that the hypodermal tissue in the open loop 9 is restored, the root portion 2 is completely retained by the hypodermal tissue 12 so that the treated hair implanted can be prevented from falling out.

Especially, the size of the intersection 4 of the treated hair according to the present invention is so small in thickness in comparison with that of the root portion according to the other methods that the wound caused during the implanting operation can be reduced in size, that few treated hairs can come out immediately after the operation and that the tissues can be restored soon. As a result, the treated hair according to the present invention can enjoy the advantage that its fixity is markedly high.

Moreover, the root portion of the artificial hair of the present invention made by forming the loop and fusing the hair at the intersection point has an adequate joint intensity at the intersection so as to remain in place under normal conditions, but the fused intersection is weaker than the strength of the hair itself so that when the implanted hair is pulled strongly, then the fused intersection will break and the implanted hair will be pulled out from the scalp together with the root portion without damage to the scalp. This is in contradistinction to artificial hair formed by knotting or otherwise where the root does not have a weakened portion; in such cases, i.e. where the root has a high joint intensity, the loop of the root portion is hard to break when the implanted hair is pulled up strongly, and in such a case the hair breaks off leaving the root portion implanted or possibly pulling the root through the scalp to make a relatively large opening in the scalp. In the former case, the remaining root portions in the scalp causes a highly serious deficit involving suppuration or edema of the scalp, and in the latter case serious damage to the scalp occurs.

Therefore, it is an important advantage of the present invention that the loop portion has an adequate intensity at the intersection so as to break the loop when the implanted hair is pulled up strongly with an intensity in the range of about 100-200 grams force, preferable 110-120 grams force, whereby the fused portion of the loop will break and the implanted hair including the root will be pulled out cleanly through the opening through which the hair protruded, thereby avoiding various impediments caused by leaving a root in the human scalp.

The foregoing description of specific embodiments of the invention will so fully revise the general nature of the invention that others can, by applying current knowledge, readily modify and/or adapt for various applications such specific embodiments without departing from the generic concept, and therefore, such adaptations and modifications should and are intended to be comprehended within the meaning and range of equivalents of the disclosed embodiments. It is to be understood that the phrasiology or terminology employed herein is for the purpose of description and not of limitation.

What is claimed is:

1. A hair for implantation comprising: an extended body portion and a relatively short unknotted root portion adapted to be implanted beneath the surface of the human skin, said root portion comprising:

a strand forming a generally water-droplet shaped open loop, said strand crossing itself and being adhered to itself by high frequency point welding at the crossing point, which crossing point is located at the top of said loop, and a free end hook portion projected upwardly from said crossing point at a acute angle, said strand having sufficient rigidity to maintain said acute angle.

2. A hair for implantation according to claim 1, consisting of thermoplastic synthetic resin.

3. A hair for implantation according to claim 2, wherein said thermoplastic synthetic resin is selected from the group consisting of polyester, polypropyene, polyethylene and polyvinyl chloride.

4. A treated hair for implanation according to claim 1, formed of two strands fixed in parallel to each other at said root portion, but separated substantially along the remainder thereof.

5. A treated hair for implantation according to claim 4, wherein the end portions of said looped portion are made to protrude between the hair components of said root portions.

6. A hair according to claim 1, wherein the strength of adhesion at said crossing point is such that said loop will break at said crossing point if said hair is subjected to a pulling force in the range of 110–120 grams.

7. A hair for implantation comprising: an extended body portion and a relatively short unknotted root portion adapted to be implanted beneath the surface of the human skin, said root portion comprising:

a strand forming a generally water-droplet shaped open loop, said strand crossing itself and being adhered to itself by high frequency point welding at the crossing point, which crossing point is located at the top of said loop, and a free end hook portion projected upwardly from said crossing point at an acute angle, the maximum and minimum outside diameters of the looped portions being 0.65 to 1.5 mm and 0.4 to 1.1 mm, respectively, and the length of said free end hook portion being 0.4 to 1.2 mm.

8. A hair for implantation comprising: an extended body portion and a relatively short unknotted root portion adapted to be implanted beneath the surface of the human skin, said root portion comprising:

a strand forming a generally water-droplet shaped open loop, said strand crossing itself and being adhered to itself by welding at the crossing point, which crossing point is located at the top of said loop, and a free end hook portion projected upwardly from said crossing point at an acute angle, said strand having sufficient rigidity to maintain said acute angle, the strength of adhesion at said crossing point being such that said loop will break at said crossing point if said hair is subjected to a pulling force in the range of 100–200 grams.

* * * * *